United States Patent [19]

Brush et al.

[11] 4,361,926

[45] Dec. 7, 1982

[54] CAUTERY CLEANING DEVICE

[76] Inventors: Claire Brush, 631 N. 62nd St., Omaha, Douglas County, Nebr. 68132; Keith M. McCormick, 1822 N. 100th St., Omaha, Douglas County, Nebr. 68114; B. J. Moor, 2029 S. 146 Cir., Omaha, Douglas County, Nebr. 68144

[21] Appl. No.: 226,296

[22] Filed: Jan. 19, 1981

[51] Int. Cl.³ .............................................. A61B 17/32
[52] U.S. Cl. .................................. 15/236 R; 15/246; 30/128; 128/305
[58] Field of Search ...................... 15/236 R, 246, 245; 128/303.14, 303.17, 305, 276; 30/128

[56] References Cited

U.S. PATENT DOCUMENTS

| | | | |
|---|---|---|---|
| 438,953 | 10/1890 | Shaw | 30/128 |
| 520,818 | 6/1894 | Bettinger | 15/236 R |
| 1,280,835 | 10/1918 | Preston | 30/128 |
| 2,140,209 | 12/1938 | Rietveld | 15/236 |
| 2,291,128 | 7/1942 | Yarrow | 30/138 |
| 2,337,158 | 12/1943 | Frank | 30/138 |
| 3,982,357 | 9/1976 | Eldridge et al. | 51/181 R |
| 4,011,693 | 5/1977 | Eldridge, Jr. et al. | 51/354 |
| 4,124,915 | 11/1978 | Schlicher | 15/236 R |
| 4,170,234 | 10/1979 | Graham | 128/303.14 |
| 4,307,720 | 12/1981 | Weber, Jr. | 128/276 |

*Primary Examiner*—Edward L. Roberts
*Attorney, Agent, or Firm*—Henderson & Sturm

[57] ABSTRACT

A cautery cleaning device including a thumb and fingertip manipulated support member with rubber-like properties through which a cautery blade is guided and in which scraping edges are supported and held in contact with the blade. The support member is conformed to fit onto the cautery pencil end adjacent the blade and is removably tethered thereto.

9 Claims, 9 Drawing Figures

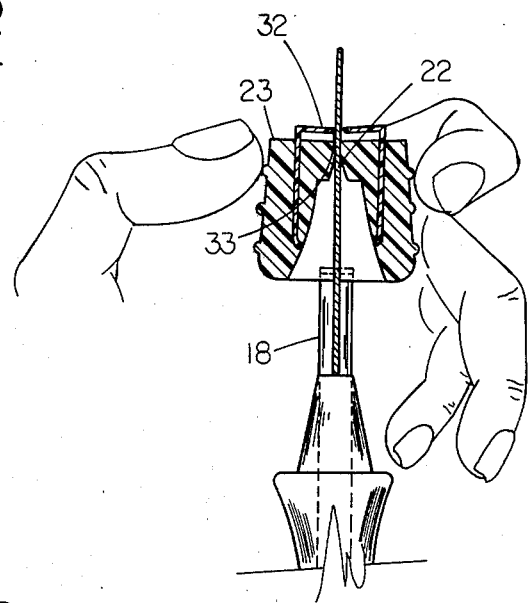
FIG. 7a
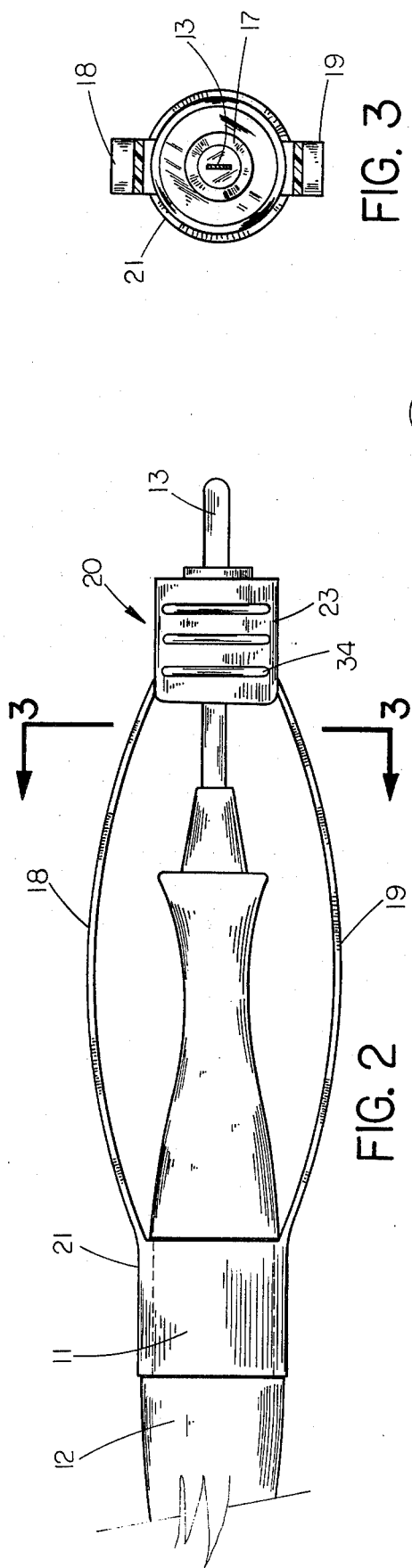
FIG. 3
FIG. 2
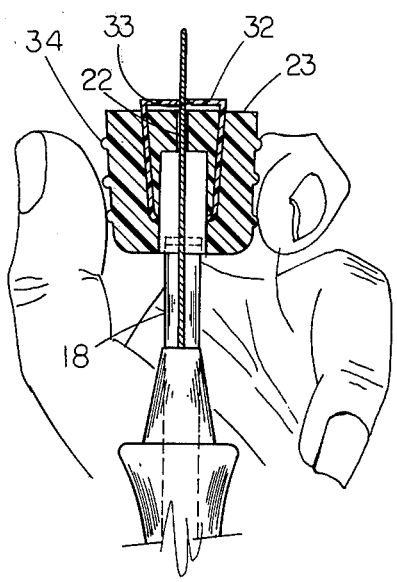
FIG. 7b

CAUTERY CLEANING DEVICE

BACKGROUND OF THE INVENTION

The present invention relates generally to devices which are attached to a handle or supporting structure for a blade for the purpose of cleaning said blade by scraping, and more particularly to such a device for cleaning a surgical cautery blade.

Cautery pencils are used in surgical procedures primarily for two purposes. One is to sever blood vessels and the other is to stop the flow of blood from severed vessels by sealing them off. To accomplish these ends a cautery pencil is wired to an electrical power source which is employed to emit high frequency radio waves from the tip of the cautery blade. When the surgeon is using the instrument to sever a vessel a higher frequency is employed.

One of the problems associated with the use of a cautery pencil for both functions is the accumulation of dried and carbonized tissue and blood on the cautery blade. Probably the most common method of cleaning a surgical cautery pencil during its use is for the surgeon or a nurse to use sandpaper pinned to the patient's gown. U.S. Pat. No. 3,982,357, teaches the use of a supporting frame attached to a towel or drape, said frame containing compressible pads which hold a pair of abrasive strips which are mutually engaging except at one end where a cautery blade is received for cleaning. Although the use of sandpaper or other abrasive materials located in the vicinity of the operating surgeon has generally been acceptable, all of the well known problems associated therewith are present. Some of these are the loss of effectiveness of the abrasive material during use through filling with removed debris, the lack of amenability to sanitizing for re-use, the removal of blade surface along with debris, and the loss of potentially valuable instants of time while the surgeon hands the pencil in need of cleaning to an aid to await for a replacement or alternatively stops to search for the cleaning implement if he elects to clean the blade himself.

SUMMARY OF THE INVENTION

The instant invention includes a thumb fingertip manipulated support member with rubber-like properties through which a cautery blade is guided and in which are supported scraping edges which push or pop off the cautery blade dried and carbonized accumulations of tissue and blood. The support member may be removably attached to the support structure of the cautery pencil adjacent the blade and tethered thereto.

An object of the present invention is the provision of an improved cautery cleaning device.

An additional object of the present invention is the provision of a cautery cleaning device which can be effectively sanitized and re-used.

Another object of the present invention is the provision of a cautery cleaning device which will not lose its effectiveness while it is used during a single surgical procedure.

A further object of the present invention is the provision of a cautery cleaning device which will not tend to wear down the blade surfaces while it is being used.

Still another object of the present invention is to provide a cautery cleaning device which is not located remote from the cautery pencil.

Yet another object of the present invention is to provide a cautery cleaning device which a surgeon may himself use with a minimum of interruption to the on-going surgical procudure.

Other objects, advantages and novel features of the present invention will become apparent from the following detailed description of the invention when considered in conjunction with the accompanying drawings.

BRIEF DESCRIPTION OF THE DRAWINGS

FIG. 2 is a partial elevational view of a typical cautery pencil with the present invention shown anchored thereto;

FIG. 3 is a cross-sectional view taken through line 3—3 of FIG. 2;

FIG. 7a is a cross-sectional view taken through line 7—7 of FIG. 5 and depicting an operator using the device while holding it towards its upper end; and FIG. 7b is a cross-sectional view taken through line 7—7 of FIG. 5 and depicting an operator using the device while holding it towards its lower end.

DESCRIPTION OF THE PREFERRED EMBODIMENT

Figure 1:
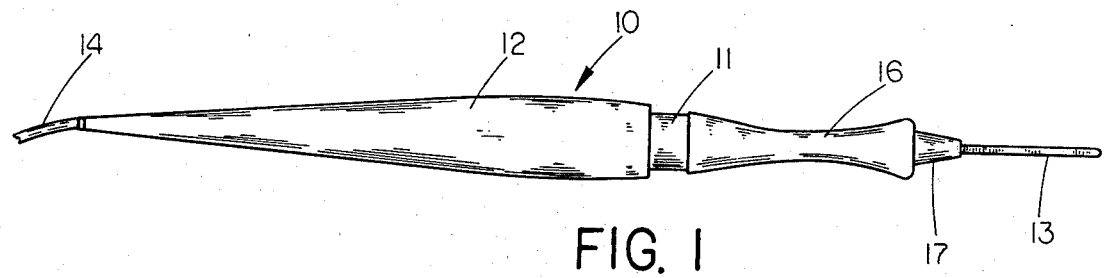
FIG. 1 is a plan view of a typical electrical cautery pencil with the inclusion of a constriction for anchoring the present invention thereto.

Referring now to the drawings, wherein like reference numerals designate identical or corresponding parts throughout the several views, FIG. 1 shows a slightly modified, but otherwise typical cautery pencil, which is designated generally at 10. Cautery 10 is modified by having a constricted portion 11 a slight distance back along stem 12 from blade 13. The purpose for constricted portion 11 will be explained later. In all other respects, cautery 10 is quite typical having a power source 14 attached at an end opposite its blade, a neck portion 16 for thumb and finger control, and a base member 17 to support blade 13.

Figure 4:
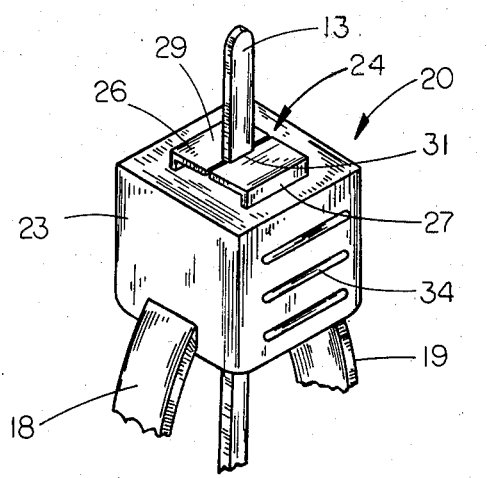
FIG. 4 is a partial perspective view of the present invention shown mounted on a cautery blade.
Figure 5:
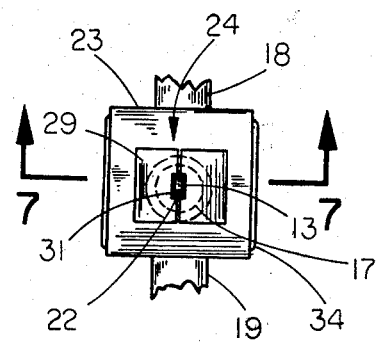
FIG. 5 is a partial end view of the present invention shown mounted on a cautery blade.
Figure 7:
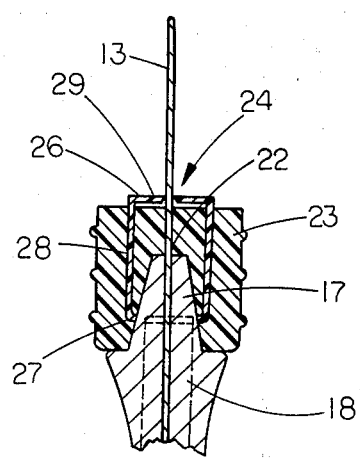
FIG. 7 is a cross-sectional view taken through line 7—7 of FIG. 5.

Referring now to FIGS. 2 and 4, the cleaning device of this invention is designated generally at 20 and is shown in its cleaning position along blade 13. Cleaning device 20 is tethered to cautery 10 by flexible tethers 18 and 19 which extend from anchor collar 21 (See FIGS. 2 and 3). Anchor collar 21 is sized so as to cooperate with constricted portion 11 and is made of a semielastic material which enables it to be forced over any enlargement along stem 12 which may be between blade 13 and constricted portion 11 of stem 12 and then be seated into constricted portion 11. As can be seen in FIGS. 5 and 7, cleaning device 20 has blade guide 22 centered longitudinally through its support member 23. To mount cleaning device 20 onto cautery 10, blade 13 is entered first through anchor collar 21 and then through guide 22 so that anchor collar 21 may be forced over stem 12 and seated in constricted portion 11.

Figure 6:
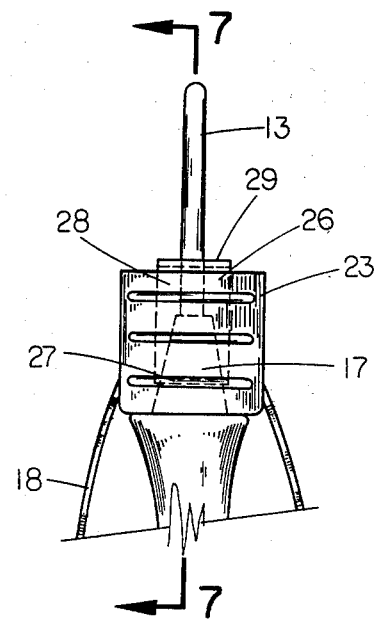
FIG. 6 is a partial side elevational view of the present invention shown mounted on a cautery blade.

Referring now to FIGS. 5, 6 and 7, it can be further noted that guide 22 has a cross-section with conforming and slightly larger dimensions than those of the cross-section of blade 13. Thus, support member 23 is generally limited to longitudinal orientation as it slides along blade 13. This limitation is designated as general because support member 23 is made of rubber, a plastic with rubber-like physical properties or any similar material in terms of its flexibility and elasticity, thus permitting some variation from a strictly longitudinal orientation. The degree and nature of such properties are to be similar to those of a rubber pencil eraser. These properties are important for several reasons which will be appreciated and explained as support member 23 is further described below. Plastics which have suitable characteristics are well known. Such materials which are also amenable to being sanitized for re-use are also well known, and it is suitable for collar 21, tethers 18 and 19, and support member 23 to be formed in one injection molding process.

Referring again to FIGS. 5, 6 and 7, the bottom of support member 23, which will be adjacent base member 17 when cleaning device 20 is mounted as aforesaid, is shaped and sized to conform to said base member 17. Support member 23, being of rubber-like material, may thus be forceably and operably seated onto base member 17 when the surgeon is using cautery 10 for sealing or cutting. Likewise, it may be easily removed from base member 17 and manually slid allong blade 13 for cleaning purposes.

Imbedded and anchored into support member 23 is scraping member 24 which is comprised of two identical half-portions 26 (see also FIG. 4). In cross-section each half-portion 26 is an inverted L, one a mirror-image of the other, (See FIG. 7) when support member 23 is mounted as aforesaid on blade 13 and the cautery 10 is oriented vertically. In this position, half-portions 26 can each be seen to have a stubby projection 27 which anchors them into a conforming and cooperating recess in support member 23. Vertical leg 28 is also within a conforming and cooperating recess which, however, is slightly shorter than vertical leg 28 in order that horizontal leg 29 will be spaced away from and above the top of support member 23. Half-portions 26 are located equidistant from and longitudinally centered with respect to blade 13.

Due to the rubber-like properties of support member 23, each half-portion 26 can be forcibly inserted into support member 23 by inserting its end which bears projection 27 through the upper end of the conforming and cooperating recess for retaining vertical leg 28 until projection 27 drops into its conforming and cooperating recess.

As can be seen in FIG. 7, horizontal segment 29 of the inverted L of each half-portion 26 is of such a length that it will have a scraping edge in contact with blade 13 when so inserted and when cleaning device 20 is mounted as aforesaid. In order that scraping member 24 can contact all four sides of blade 13 each half portion 26 has a horizontal U-shaped notch 31 for contact with its adjacent one-half of the cross-sectional perimeter of blade 13. To further promote the effectiveness of scraper 26 a pointed horizontal edge is formed by the intersection of the upper side 32 of horizontal segment 29 and the shallow vertical side 33 which forms notch 31. Shallow side 33 is at an angle to the vertical in order that it will form with upper side 32 an acute angle of approximately 70°. See also FIGS. 7a and 7b.

Referring once again to FIGS. 7a and 7b, the full value of the flexibility and elasticity of main body 23 can be appreciated. Note how the angle of contact of scraper 24 with blade 13 can be varied in the plane depicted in said FIGS. 7a and 7b. Fingertip control is further enhanced by a plurality of horizontal ribs 34 which are formed as part of support member 23 and located on its sides. By a squeezing and rocking motion aided by the fulcrum effect of the varying area of contact between guide 22 and blade 13, a great degree of scraping force can be generated against all four sides of blade 13. The application of this force can also be varied as to degree and angle due to the rubber-like properties of support member 23. As scraper 24 is worked up and down blade 13 and made to contact any of its four sides with the desired force and at the desired angle, the debris clinging to blade 13 is pushed and popped free thereof.

Obviously, many modifications and variations of the present invention are possible in light of the above teachings. It is therefore to be understood that, within the scope of the appended claims, the invention may be practiced otherwise than as specifically described.

I claim:

1. A device for cleaning the blade of a cautery pencil, comprising:
    means for scraping foreign matter from the cautery blade; and
    means of rubber-like material surrounding the blade for mounting the device onto the blade, guiding the scraping means longitudinally along the blade and supporting the scraping means against the blade in order that the angles of contact of the scraping means against the cautery blade may be dexterously controlled.

2. A cleaning device as recited in claim 1 wherein the scraping means includes two opposing portions located on either side of the blade in order that two sides of the cautery blade may be simultaneously cleaned.

3. A cleaning device as recited in claim 2 wherein the two scraping means portion(s) each have opposing notches of such shape that when the scraping means is supported against the blade all sides of the blade will be substantially contacted in order that all sides of the cautery blade may be cleaned more or less simultaneously.

4. A cleaning device as recited in claim 3 wherein the edge of each scraping means portion, which contacts a broad side of a rectangular section cautery blade, is characterized as being formed by two planar surfaces which intersect at an acute angle of approximately 70°, said scraper means being supported against the blade such that the planar surface which is distal the cautery blade holder is substantially oriented normal to the cautery blade when the cleaning device is mounted on the cautery blade.

5. A cleaning device as recited in claim 1 wherein the piece of rubber-like material comprising the scraping means mounting, guiding and supporting means is conformed at one end so as to conformably and removably sit on a cautery blade base member of a cautery implement whereby it will remain seated when it is not being used to clean.

6. A cleaning device as recited in claim 5 further comprising means for tethering the cleaning device to the cautery implement.

7. A cleaning device as recited in claim 6 wherein said tethering means is further characterized by being of such length that the guide means will not be able to slip off the cautery blade.

8. A cleaning device as recited in claim 7 wherein the tethering means further comprises means for operably anchoring it to the cautery implement and means for receiving said anchor means on the cautery implement.

9. A cleaning device as recited in claim 8 wherein the tethering means, the anchoring means and the supporting means are made of one piece of flexible elastic material.

* * * * *